(12) United States Patent
Mironov

(10) Patent No.: US 10,136,673 B2
(45) Date of Patent: Nov. 27, 2018

(54) ELECTRICALLY HEATED AEROSOL-GENERATING SYSTEM

(71) Applicant: Philip Morris Products S.A., Neuchatel (CH)

(72) Inventor: Oleg Mironov, Neuchatel (CH)

(73) Assignee: PHILIP MORRIS PRODUCTS S.A., Neuchatel (CH)

( * ) Notice: Subject to any disclaimer, the term of this patent is extended or adjusted under 35 U.S.C. 154(b) by 252 days.

(21) Appl. No.: 15/128,787

(22) PCT Filed: Mar. 17, 2015

(86) PCT No.: PCT/EP2015/055590
§ 371 (c)(1),
(2) Date: Sep. 23, 2016

(87) PCT Pub. No.: WO2015/150068
PCT Pub. Date: Oct. 8, 2015

(65) Prior Publication Data
US 2018/0213843 A1   Aug. 2, 2018

(30) Foreign Application Priority Data
Mar. 31, 2014 (EP) .................................. 14162938

(51) Int. Cl.
*A24F 47/00* (2006.01)
*H05B 6/06* (2006.01)
(Continued)

(52) U.S. Cl.
CPC ........... *A24F 47/008* (2013.01); *A61M 15/06* (2013.01); *H05B 6/06* (2013.01); *A61M 2205/13* (2013.01);
(Continued)

(58) Field of Classification Search
None
See application file for complete search history.

(56) References Cited

U.S. PATENT DOCUMENTS

2006/0196518 A1   9/2006   Hon
2012/0048266 A1   3/2012   Alelov
(Continued)

FOREIGN PATENT DOCUMENTS

EP         1 618 803 B1    12/2008
WO      2013/147492 A1    10/2013

OTHER PUBLICATIONS

International Search Report and Written Opinion dated Jun. 30, 2015 in PCT/EP2015/055590 Filed Mar. 17, 2015.

*Primary Examiner* — Eric Yaary
(74) *Attorney, Agent, or Firm* — Oblon, McClelland, Maier & Neustadt, L.L.P.

(57) ABSTRACT

An electrically operated aerosol-generating system is provided, including a housing; an aerosol-forming substrate; at least one heating element configured to heat the aerosol-forming substrate and to generate an aerosol; a power supply configured to supply power to the at least one heating element; electric circuitry configured to control a supply of power from the power supply to the at least one heating element; a first switch provided on an external surface of the housing; and a mouthpiece including at least one second, touch sensitive, switch, the mouthpiece being deformable from a first configuration to a second configuration, wherein in the first configuration the at least one second switch is not exposed and in the second configuration the at least one second switch is exposed. The circuitry is configured to provide power to the at least one heating element when both the first switch and the second switch are activated.

15 Claims, 1 Drawing Sheet

Figure 1A:
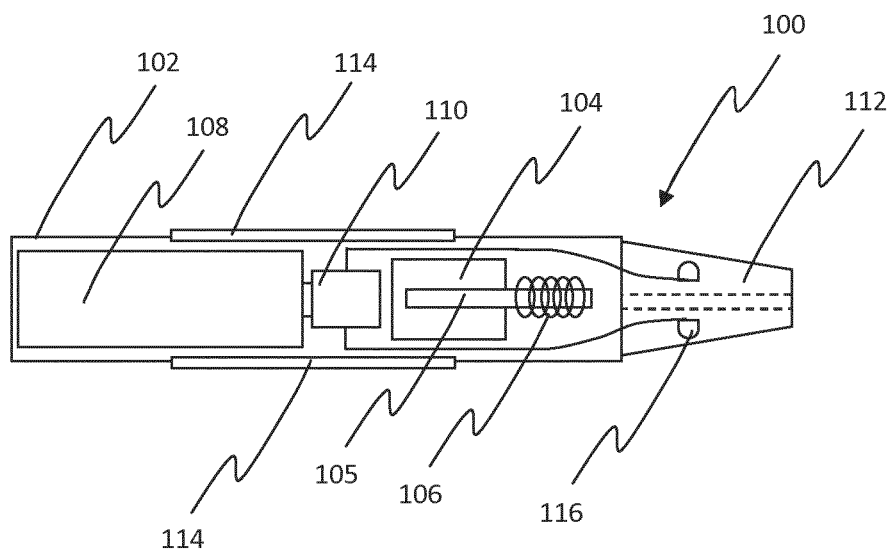

(51) Int. Cl.
*A61M 15/06* (2006.01)
*H03K 17/96* (2006.01)

(52) U.S. Cl.
CPC . *A61M 2205/3653* (2013.01); *H03K 17/9622* (2013.01); *H03K 17/9647* (2013.01)

(56) References Cited

U.S. PATENT DOCUMENTS

| | | |
|---|---|---|
| 2012/0090630 A1 | 4/2012 | Hon |
| 2012/0227752 A1 | 9/2012 | Alelov |
| 2012/0273589 A1 | 11/2012 | Hon |
| 2013/0213418 A1 | 8/2013 | Tucker et al. |
| 2013/0239957 A1 | 9/2013 | Pinfold |
| 2013/0247924 A1 | 9/2013 | Scatterday et al. |
| 2013/0276804 A1 | 10/2013 | Hon |
| 2013/0284190 A1 | 10/2013 | Scatterday et al. |
| 2013/0284191 A1 | 10/2013 | Scatterday et al. |
| 2014/0060527 A1 | 3/2014 | Liu |
| 2014/0060554 A1 | 3/2014 | Collett et al. |
| 2014/0224245 A1 | 8/2014 | Alelov |
| 2014/0261499 A1 | 9/2014 | Hon |
| 2014/0318560 A1 | 10/2014 | Hon |
| 2014/0334804 A1 | 11/2014 | Choi |
| 2015/0027459 A1 | 1/2015 | Collett et al. |

ELECTRICALLY HEATED AEROSOL-GENERATING SYSTEM

The present invention relates to an electrically heated aerosol-generating system for generating an aerosol. The invention also relates to an associated aerosol-generating device and article. In particular, the invention relates to an electrically heated aerosol-generating system having at least two switches for activating the electrical heater.

Electrically heated aerosol-generating devices and systems for providing users with a smoking experience are well known. In general, two types of system are known, either the electrical heater is activated for an entire smoking experience or the electrical heater is activated each time a user puffs on the device. In the latter type, various means are known to activate the heater when a puff is detected, including for example microphones, pressure sensors, and changes in heater coil resistivity. These types of puff sensor are associated with the potential for false detection of puffs, for example when the device is moving or in windy conditions.

To overcome the problem of false puff detection, a number of systems have been developed. EP 1 618 803 B1 discloses an electrically operated aerosol-generating system comprising a "body sensitive sensor" to control the operation of the system to replace an airflow sensor. The "body sensitive sensor" can be a resistance sensor or a capacitance sensor, and the system is activated, and a vapour generated, when the sensor is activated by the user placing the device in their mouth. US 2013/0239957 A1 discloses a similar "lip sensor" for detecting when a user's lips are in contact with a mouthpiece and triggering the system to release an aerosol. However, in this disclosure, the "lip sensor" is a mechanical switch activated by pressure from the user's lips.

Although these prior art system mitigate against the false detections which occur when using a puff detector, the lip sensors of EP 1 618 803 B1 and US 2013/0239957 A1 do not always mitigate against false activation of the electrical heater. For example, such lip sensors may still be activated when a user is withdrawing the device from a bag, or when picking the device up because the sensors cannot distinguish between fingers and lips, they merely sense touch.

It is therefore an object of the present invention to provide an electrically heated aerosol-generating device having an improved activation sensor for preventing false activation of the device. It is a further object of the invention to provide such an improved sensor without impinging on the user experience.

According to the present invention there is provided, an electrically operated aerosol-generating system. The system comprises: a housing; an aerosol-forming substrate; at least one heating element for heating the aerosol-forming substrate to generate an aerosol; a power supply for supplying power to the at least one heating element; electric circuitry for controlling supply of power from the power supply to the at least one heating element; a first switch provided on an external surface of the housing; and a mouthpiece comprising at least one second, touch sensitive, switch, the mouthpiece being deformable from a first configuration to a second configuration, wherein in the first configuration the at least one second, touch sensitive, switch is not exposed and in the second configuration the at least one second, touch sensitive, switch is exposed. The circuitry is arranged to provide power to the at least one heating element when both the first switch and the second, touch sensitive, switch are activated.

Advantageously, providing a system having two switches which must be activated before the system is enabled reduces the risk of the system being activated accidentally. The use of a deformable mouthpiece to enable one of the switches to remain covered until the user places the mouthpiece in their mouth yet further reduces the risk of the system being activated accidentally.

In addition, having two switches to activate the at least one heating element whereby one of the switches is activated by the user placing the system in their mouth, the time lag between requiring an aerosol to be formed, and the aerosol being formed, may be reduced as compared to a system which incorporates more conventional puff detectors which require the user to begin drawing on the system before it is activated.

By removing conventional puff detectors to activate the heating element, the system may be less complex, and will reduce the requirement for maintenance of the puff detection system. A conventional puff detection system necessarily is within the airflow pathway which includes the aerosol, and as such may be contaminated by the aerosol reducing its efficacy, and the time between maintenance or replacement.

The aerosol-generating system may comprise an aerosol-generating device comprising the housing, the at least one heating element, the power supply, the electric circuitry and the mouthpiece, and an aerosol-generating article comprising the aerosol-forming substrate. Alternatively, the aerosol-generating article may comprise at least one heating element, and the aerosol-forming substrate. When the system comprises an aerosol-generating device, the housing of the device preferably comprises a cavity for receiving the aerosol-generating article. In this or a further alternative, the aerosol-generating article may comprise the mouthpiece.

As used herein, the term "mouthpiece" refers to a portion of the aerosol-generating system, aerosol-generating article, or aerosol-generating device, that is placed into a user's mouth in order to directly inhale an aerosol generated by the aerosol-generating system.

The housing of the aerosol-generating system is the outer body, i.e. the part that is held by the user.

In a preferred embodiment, the first switch is a touch sensitive switch. Alternatively, the first switch may be a mechanical switch, such as a push button biased switch, a slider switch, a toggle switch or any other suitable type of switch.

In the preferred embodiment, the first, touch sensitive, switch may extend along at least 30% of the length of the housing. The first, touch sensitive, switch may extend along at least 50% of the length of the housing, at least 75% of the housing or the entire length of the housing. The first, touch sensitive, switch may be provided substantially at the midpoint along the longitudinal length of the housing. By providing the switch in this location along the length of the housing, the user may more naturally activate the switch without undue effort.

As used herein, the term "length" refers to the longitudinal length of the housing from a first distal end to a second proximal end.

The touch sensitive switches may be a capacitive switch or a resistive switch. A capacitive switch comprises a single electrode, and the capacitance of the human body to determine when the switch has been touched. A resistive switch comprises two electrodes, and the resistance of the human body to determine when a finger, for example, is connecting both electrodes to form a complete circuit.

In one preferred embodiment, the second, touch sensitive, switch is a resistive switch comprising two electrodes. The electrodes are preferably disposed on diametrically opposite sides of the mouthpiece, and preferably. The electrodes are preferably in the form of studs, having a dome shape. The electrodes are preferably recessed within the deformable mouthpiece, and are not exposed to be touched, and therefore activated, until the user places the mouthpiece in their mouth and applies a force to deform the mouthpiece into the second configuration.

In this embodiment, the force required to deform the mouthpiece from the first configuration to the second configuration is sufficient to deform the thickness of the mouthpiece by at least about 10%. Preferably, the force required is sufficient to deform the mouthpiece such that at least one touch sensitive switch is exposed.

In a particularly preferred embodiment, the mouthpiece is provided with a resilience equivalent to a conventional cigarette or cigar, and as such the user may be provided with an improved usage experience.

The system may further comprise a third switch. The third switch is preferably a mechanical switch to enable the user to completely disable the system. The third switch may be a slider switch, a toggle switch, a push button switch or any other suitable mechanical switch.

The electric circuitry may be further arranged to control the supply of power from the power supply to the at least one heating element in a pre-heating mode. The pre-heating mode may comprise a spike of power. The spike of power preferably further reduces the time lag between the user requiring an aerosol to be generated and the aerosol being generated. The time lag is reduced by enabling the heater to heat the aerosol-generating substrate to the operation temperature more quickly.

The initial spike of power may be between 125% and 200% of the continuous power provided to the heating element in the normal heating mode. The level of power provide in the pre-heating mode may be dependent on operational parameters such as the ambient conditions including temperature, and humidity, and on the type of aerosol-generating substrate being heated.

In one embodiment, the electric circuitry may be further arranged to initiate the pre-heating mode when the first switch is activated, and before the second, touch sensitive, switch is activated. The electric circuitry thus may be further arranged to provide power to the at least one heating element in a heating mode when the second, touch sensitive, switch is activated subsequent to the controller providing power to the at least one heating element in the pre-heating mode.

The or each at least one heating element may be an inductive heating element. The present invention is of particular benefit when the heating element is an inductive heating element. Conventional puff detection systems often involve the use of detecting changes in heater element resistance when the user puffs on the device. However, such puff detection is not possible when using an inductive heater.

The electric circuitry may comprise a microcontroller. The microcontroller may include a PID regulator for controlling the power supplied to the heating element. The PID regulator may ensure that the temperature of the aerosol-forming substrate is kept at or below the operational temperature.

The system may comprise more than one heating element, for example two, or three, or four, or five, or six or more heating elements. The heating element or heating elements may be arranged appropriately so as to most effectively heat the aerosol-forming substrate.

The at least one electric heating element preferably comprises an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, Constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation, 1999 Broadway Suite 4300, Denver Colo. In composite materials, the electrically resistive material may optionally be embedded in, encapsulated or coated with an insulating material or vice-versa, depending on the kinetics of energy transfer and the external physicochemical properties required. The heating element may comprise a metallic etched foil insulated between two layers of an inert material. In that case, the inert material may comprise Kapton®, all-polyimide or mica foil. Kapton® is a registered trade mark of E.I. du Pont de Nemours and Company, 1007 Market Street, Wilmington, Del. 19898, United States of America.

Alternatively, the at least one electric heating element may comprise an infra-red heating element, a photonic source, or as described above an inductive heating element.

The at least one electric heating element may take any suitable form. For example, the at least one electric heating element may take the form of a heating blade. Alternatively, the at least one electric heating element may take the form of a casing or substrate having different electro-conductive portions, or an electrically resistive metallic tube. If the aerosol-forming substrate is a liquid provided within a container, the container may incorporate a disposable heating element. Alternatively, one or more heating needles or rods that run through the centre of the aerosol-forming substrate may also be suitable. Alternatively, the at least one electric heating element may be a disk (end) heating element or a combination of a disk heating element with heating needles or rods. Alternatively, the at least one electric heating element may comprise a flexible sheet of material arranged to surround or partially surround the aerosol-forming substrate. Other alternatives include a heating wire or filament, for example a Ni—Cr, platinum, tungsten or alloy wire, or a heating plate. Optionally, the heating element may be deposited in or on a rigid carrier material.

The at least one electric heating element may comprise a heat sink, or heat reservoir comprising a material capable of absorbing and storing heat and subsequently releasing the heat over time to the aerosol-forming substrate. The heat sink may be formed of any suitable material, such as a suitable metal or ceramic material. Preferably, the material has a high heat capacity (sensible heat storage material), or is a material capable of absorbing and subsequently releasing heat via a reversible process, such as a high temperature phase change. Suitable sensible heat storage materials include silica gel, alumina, carbon, glass mat, glass fibre, minerals, a metal or alloy such as aluminium, silver or lead, and a cellulose material such as paper. Other suitable materials which release heat via a reversible phase change include paraffin, sodium acetate, naphthalene, wax, polyethylene oxide, a metal, metal salt, a mixture of eutectic salts or an alloy.

The heat sink or heat reservoir may be arranged such that it is directly in contact with the aerosol-forming substrate and can transfer the stored heat directly to the substrate. Alternatively, the heat stored in the heat sink or heat reservoir may be transferred to the aerosol-forming substrate by means of a heat conductor, such as a metallic tube.

The at least one heating element may heat the aerosol-forming substrate by means of conduction. The heating element may be at least partially in contact with the substrate, or the carrier on which the substrate is deposited. Alternatively, the heat from the heating element may be conducted to the substrate by means of a heat conductive element.

Alternatively, the at least one heating element may transfer heat to the incoming ambient air that is drawn through the electrically heated aerosol generating system during use, which in turn heats the aerosol-forming substrate by convection. The ambient air may be heated before passing through the aerosol-forming substrate. Alternatively, if the aerosol-forming substrate is a liquid substrate, the ambient air may be first drawn through the substrate and then heated.

The aerosol-forming substrate may be a solid aerosol-forming substrate. The aerosol-forming substrate preferably comprises a tobacco-containing material containing volatile tobacco flavour compounds which are released from the substrate upon heating. The aerosol-forming substrate may comprise a non-tobacco material. The aerosol-forming substrate may comprise tobacco-containing material and non-tobacco containing material. Preferably, the aerosol-forming substrate further comprises an aerosol former. Examples of suitable aerosol formers are glycerine and propylene glycol.

Alternatively, the aerosol-forming substrate may be a liquid aerosol-forming substrate. In one embodiment, the electrically heated aerosol generating system further comprises a liquid storage portion. Preferably, the liquid aerosol-forming substrate is stored in the liquid storage portion. In one embodiment, the electrically heated aerosol generating device further comprises a capillary wick in communication with the liquid storage portion. It is also possible for a capillary wick for holding liquid to be provided without a liquid storage portion. In that embodiment, the capillary wick may be preloaded with liquid.

Preferably, the capillary wick is arranged to be in contact with liquid in the liquid storage portion. In that case, in use, liquid is transferred from the liquid storage portion towards the at least one electric heating element by capillary action in the capillary wick. In one embodiment, the capillary wick has a first end and a second end, the first end extending into the liquid storage portion for contact with liquid therein and the at least one electric heating element being arranged to heat liquid in the second end. When the heating element is activated, the liquid at the second end of the capillary wick is vaporized by the heating element to form the supersaturated vapour. The supersaturated vapour is mixed with and carried in the airflow. During the flow, the vapour condenses to form the aerosol and the aerosol is carried towards the mouth of a user. The heating element in combination with a capillary wick may provide a fast response, because that arrangement may provide a high surface area of liquid to the heating element. Control of the heating element according to the invention may therefore depend on the structure of the capillary wick arrangement.

The liquid substrate may be absorbed into a porous carrier material, which may be made from any suitable absorbent plug or body, for example, a foamed metal or plastics material, polypropylene, terylene, nylon fibres or ceramic. The liquid substrate may be retained in the porous carrier material prior to use of the electrically heated aerosol generating device or alternatively, the liquid substrate material may be released into the porous carrier material during, or immediately prior to use. For example, the liquid substrate may be provided in a capsule. The shell of the capsule preferably melts upon heating and releases the liquid substrate into the porous carrier material. The capsule may optionally contain a solid in combination with the liquid.

If the aerosol-forming substrate is a liquid substrate, the liquid has physical properties. These include, for example, a boiling point, vapour pressure, and surface tension characteristics to make them suitable for use in the aerosol generating device. Control of the at least one electric heating element may depend upon the physical properties of the liquid substrate. The liquid preferably comprises a tobacco-containing material comprising volatile tobacco flavour compounds which are released from the liquid upon heating. Alternatively, or in addition, the liquid may comprise a non-tobacco material. The liquid may include water, solvents, ethanol, plant extracts and natural or artificial flavours. Preferably, the liquid further comprises an aerosol former. Examples of suitable aerosol formers are glycerine and propylene glycol.

An advantage of providing a liquid storage portion is that a high level of hygiene can be maintained. Using a capillary wick extending between the liquid and the electric heating element, allows the structure of the device to be relatively simple. The liquid has physical properties, including viscosity and surface tension, which allow the liquid to be transported through the capillary wick by capillary action. The liquid storage portion is preferably a container. The liquid storage portion may not be refillable. Thus, when the liquid in the liquid storage portion has been used up, the aerosol generating device is replaced. Alternatively, the liquid storage portion may be refillable. In that case, the aerosol generating device may be replaced after a certain number of refills of the liquid storage portion. Preferably, the liquid storage portion is arranged to hold liquid for a pre-determined number of puffs.

The capillary wick may have a fibrous or spongy structure. The capillary wick preferably comprises a bundle of capillaries. For example, the capillary wick may comprise a plurality of fibres or threads, or other fine bore tubes. The fibres or threads may be generally aligned in the longitudinal direction of the aerosol generating device. Alternatively, the capillary wick may comprise sponge-like or foam-like material formed into a rod shape. The rod shape may extend along the longitudinal direction of the aerosol generating device. The structure of the wick forms a plurality of small bores or tubes, through which the liquid can be transported to the electric heating element, by capillary action. The capillary wick may comprise any suitable material or combination of materials. Examples of suitable materials are ceramic- or graphite-based materials in the form of fibres or sintered powders. The capillary wick may have any suitable capillarity and porosity so as to be used with different liquid physical properties such as density, viscosity, surface tension and vapour pressure. The capillary properties of the wick, combined with the properties of the liquid, ensure that the wick is always wet in the heating area.

The aerosol-forming substrate may alternatively be any other sort of substrate, for example, a gas substrate, or any combination of the various types of substrate. During operation, the substrate may be completely contained within the electrically heated aerosol generating device. In that case, a user may puff on a mouthpiece of the electrically heated aerosol generating device. Alternatively, during operation, the substrate may be partially contained within the electrically heated aerosol generating device. In that case, the substrate may form part of a separate article and the user may puff directly on the separate article.

The electrically heated aerosol generating system may comprise an aerosol-forming chamber in which aerosol forms from a super saturated vapour, which aerosol is then carried into the mouth of a user. An air inlet, air outlet and the chamber are preferably arranged so as to define an airflow route from the air inlet to the air outlet via the aerosol-forming chamber, so as to convey the aerosol to the air outlet and into the mouth of a user.

Preferably, the housing of the aerosol-generating system is elongate. The structure of the housing, including the surface area available for condensation to form, will affect the aerosol properties and whether there is liquid leakage from the device. The housing may comprise a shell and a mouthpiece. In that case, all the components may be contained in either the shell or the mouthpiece. The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle. The material of the housing may affect the amount of condensation forming on the housing which will, in turn, affect liquid leakage from the device.

Preferably, the aerosol generating system is portable. The aerosol generating system may be a smoking device and may have a size comparable to a conventional cigar or cigarette. The smoking device may have a total length between approximately 30 mm and approximately 150 mm. The smoking device may have an external diameter between approximately 5 mm and approximately 30 mm.

Any feature in one aspect of the invention may be applied to other aspects of the invention, in any appropriate combination. In particular, method aspects may be applied to apparatus aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

Figure 1B:
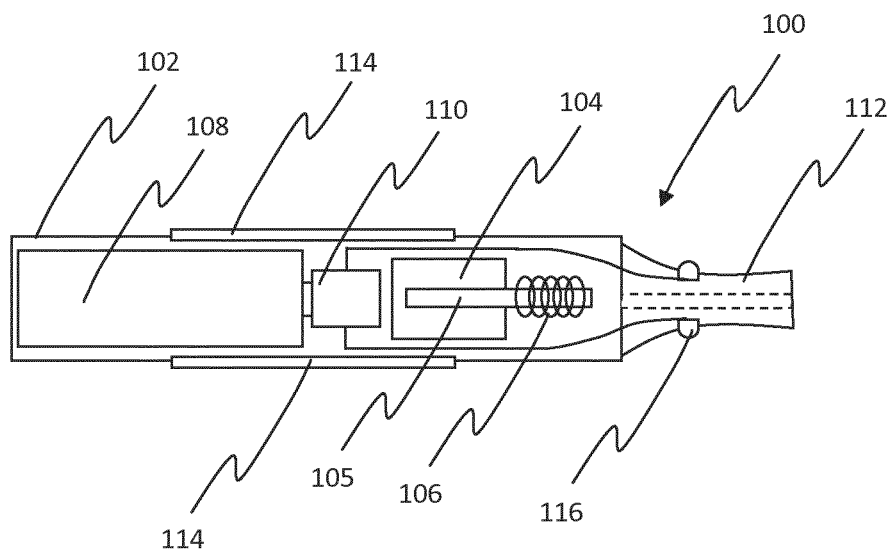

The invention will be further described, by way of example only, with reference to the accompanying drawings in which:

FIG. 1(a) shows an electrically heated aerosol-generating system in a first configuration in accordance with one embodiment of the present invention; and FIG. 1(b) shows an electrically heated aerosol-generating system in a second configuration in accordance with one embodiment of the present invention.

FIG. 1 show an electrically heated aerosol-generating system 100 comprising an outer housing 102. The housing houses a container 104 for a liquid aerosol-generating substrate, which has a capillary wick 105 and an electric heating element which is preferably a heating coil 106 adjacent an end of the wick 105, a power supply 108 which is preferably a rechargeable battery, and control circuitry 110. The system 100 further comprises a mouthpiece 112. A first, touch sensitive, switch 114 is provided on the outer surface of the housing 102, and a second, touch sensitive, switch 116 is provided in the deformable mouthpiece 112. The housing also includes an air inlet, and an air outlet at the mouthpiece end of the system.

In an alternative embodiment to the one shown in FIG. 1, the capillary wick 105 may be a U-shaped wick. In this alternative, the free ends of the wick are both extend into the container 104, and the heating element is provided substantially at the mid-point of the wick.

The circuitry 110 is arranged to control the supply of power from the power supply 108 to the electric heating element 106. The circuitry is arranged to provide power to the heating element when both the first, touch sensitive, switch 114 and the second, touch sensitive, switch 116 are activated.

The first, touch sensitive, switch 114 is a capacitive type switch, and the second, touch sensitive, switch 116 is a resistive type switch. The first switch may only have a single electrode configured to detect the capacitance of a user's body. The second switch comprises two electrodes, and a complete circuit is formed when a conductive element, such as a user's lips, is placed in contact with both electrodes as described below.

In use, operation is as follows. The user picks up the system and simply by holding the system in the region of the first, touch, sensitive switch, the switch is activated. At this stage, the circuitry 110 does not yet provide power to the heating element 106. When the user places the system in their mouth and forms a seal with their lips around the mouthpiece, the mouthpiece is deformed from a first configuration as shown in FIG. 1(a), to a second configuration as shown in FIG. 1(b). As can be seen, in the second configuration the second, touch sensitive, switch 116 is exposed, and the user's lips touch the electrodes of the switch completing the circuit. At this stage, the circuitry 110 begins to provide power from the power supply 108 to the heating element 110.

Upon heating of the heating element, liquid is transferred by capillary action from the container 104 from one end of the wick 105 which extends into the container to another end of the wick which is surrounded by the heating coil 106. When a user draws on the mouthpiece, ambient air is drawn through the air inlet. The liquid in the end of the wick surrounded by the heating element is vaporized by the heating coil 106 to create a supersaturated vapour. At the same time, the vaporized liquid is replaced by further liquid which is conveyed along the wick 105 by capillary action. This process is sometimes referred to as pumping action. The supersaturated vapour created is mixed with and carried in the air flow from the air inlet. The vapour then condenses to form an inhalable aerosol, which is carried towards the outlet and into the mouth of the user.

As described above, the mouthpiece 112 is deformable and is configured to provide a similar mouth-feel to the user as a conventional cigarette or cigar.

By requiring two switches to be activated before the system is activated reduces the risk of the system being activated accidentally. Further, having a switch within the mouthpiece, activated by the user's lips, ensures that the system is activated before a system having a more conventional puff detection system reliant on air flow through the system. Thus, the time lag between the user requiring an aerosol to be generated, and the aerosol being generated may be reduced.

FIG. 1 shows one example of an aerosol generating system which may be used with the present invention. Many other examples are usable with the invention, however. For example, the first, touch sensitive, switch may instead be a manually operated mechanical switch. The housing may also comprise a separable shell and mouthpiece. In this example, the shell may comprise the power supply, control circuitry, and first switch, and the mouthpiece may comprise the container for the aerosol-forming substrate, the heating element and the mouthpiece having the second switch.

The overall shape and size of the housing may also be altered from that shown in FIG. 1. Further, the system may be arranged so that air may enter the aerosol generating system 100 in a direction substantially perpendicular to a longitudinal axis of the aerosol generating system 100.

In one example, the circuitry 110 is arranged to provide an initial spike of power, in a pre-heating mode, from the power supply 108 to the heating element 106 to raise the temperature of the heating element to the operation temperature more quickly. The initial spike of power may be between 125% and 200% of the continuous power provided to the heating element in the normal heating mode. The level of power provided in the pre-heating mode may be dependent on operational parameters such as the ambient conditions including temperature, and humidity, and on the type of aerosol-generating substrate being heated.

In this example, the pre-heating mode may be activated by the first, touch sensitive, switch 114 alone. Therefore, as the user picks up the system the first switch is activated and power is provided to the heating element such that the heating element is already at operational temperature as the user places the mouthpiece in their mouth and begins puffing on the system.

The invention claimed is:

1. An electrically operated aerosol-generating system, comprising:
   a housing;
   an aerosol-forming substrate;
   at least one heating element configured to heat the aerosol-forming substrate and to generate an aerosol;
   a power supply configured to supply power to the at least one heating element;
   electric circuitry configured to control a supply of power from the power supply to the at least one heating element;
   a first switch provided on an external surface of the housing; and
   a mouthpiece comprising at least one second, touch sensitive, switch, the mouthpiece being deformable from a first configuration to a second configuration,
   wherein in the first configuration the at least one second, touch sensitive, switch is not exposed and in the second configuration the at least one second, touch sensitive, switch is exposed, and
   wherein the electric circuitry is configured to provide power via the power supply to the at least one heating element when both the at least one first switch and the at least one second, touch sensitive, switch are activated.

2. The system according to claim 1, wherein the at least one first switch is a touch sensitive switch.

3. The system according to claim 2, wherein the at least one first, switch extends along at least 30% of a length of the housing.

4. The system according to claim 2, wherein the at least one first switch is provided substantially at a mid-point along a longitudinal length of the housing.

5. The system according to claim 2, wherein the at least one first switch is a resistive switch or a capacitive switch.

6. The system according to claim 1, wherein the mouthpiece is configured to deform from the first configuration to the second configuration by application of a force that is sufficient to deform a thickness of the mouthpiece by at least about 10%.

7. The system according to claim 1, wherein the at least one second, touch sensitive, switch is a resistive switch or a capacitive switch.

8. The system according to claim 1, wherein the electric circuitry is further configured to control the supply of power from the power supply to the at least one heating element in a pre-heating mode.

9. The system according to claim 8, wherein the pre-heating mode comprises a spike of power.

10. The system according to claim 8, wherein the electric circuitry is further configured to initiate the pre-heating mode when the at least one first switch is activated, and before the at least one second, touch sensitive, switch is activated.

11. The system according to claim 9, wherein the electric circuitry is further configured to provide power via the power supply to the at least one heating element in a heating mode when the at least one second, touch sensitive, switch is activated subsequent to providing power to the at least one heating element in the pre-heating mode.

12. The system according to, claim 1, wherein the at least one heating element is an inductive heating element.

13. The system according to claim 1, further comprising an aerosol-generating device and an aerosol-generating article,
   the aerosol-generating device comprising:
      the housing;
      the power supply; and
      the electric circuitry, and
   the aerosol-generating article comprising:
      the aerosol-forming substrate.

14. The system according to claim 13, wherein the aerosol-generating device further comprises the mouthpiece.

15. The system according to claim 13, wherein the aerosol-generating article further comprises the mouthpiece.

* * * * *